United States Patent
Ijasan et al.

(10) Patent No.: US 12,000,279 B2
(45) Date of Patent: Jun. 4, 2024

(54) ESTIMATING PORE AND FLUID CHARACTERISTIC PROPERTIES IN ROCK SAMPLES USING NUCLEAR MAGNETIC RESONANCE ANALYSES

(71) Applicant: ExxonMobil Technology and Engineering Company, Spring, TX (US)

(72) Inventors: Olabode Ijasan, The Woodlands, TX (US); Darren M. McLendon, Houston, TX (US)

(73) Assignee: ExxonMobil Technology and Engineering Company, Spring, TX (US)

( * ) Notice: Subject to any disclaimer, the term of this patent is extended or adjusted under 35 U.S.C. 154(b) by 965 days.

(21) Appl. No.: 16/947,764

(22) Filed: Aug. 14, 2020

(65) Prior Publication Data

US 2021/0132250 A1    May 6, 2021

Related U.S. Application Data (60) Provisional application No. 62/930,275, filed on Nov. 4, 2019, provisional application No. 62/930,270, filed on Nov. 4, 2019.

(51) Int. Cl.
*G01N 24/08* (2006.01)
*E21B 7/04* (2006.01)
(Continued)

(52) U.S. Cl.
CPC ............ *E21B 49/088* (2013.01); *E21B 7/046* (2013.01); *E21B 49/02* (2013.01);
(Continued)

(58) Field of Classification Search
CPC ... G01V 3/32; G01V 3/14; G01V 3/38; G01V 5/00; G01V 5/04; G01N 24/081;
(Continued)

(56) References Cited

U.S. PATENT DOCUMENTS

| 2012/0065888 A1 | 3/2012 | Wu et al. |
| 2016/0139066 A1* | 5/2016 | Luo .......................... G01V 3/32 324/318 |

FOREIGN PATENT DOCUMENTS

WO   WO-2018208296 A1 *  11/2018  ............. E21B 47/00

OTHER PUBLICATIONS

Han Jiang, Hugh Daigle, Xiao Tian, Michael J. Pyrcz, Chris Griffith, Boyang Zhang, A comparison of clustering algorithms applied to fluid characterization using NMR T1-T2 maps of shale, Computers & Geosciences, vol. 126, (Year: 2019).*

(Continued)

*Primary Examiner* — Alvaro E Fortich
*Assistant Examiner* — Martin Walter Braunlich
(74) *Attorney, Agent, or Firm* — ExxonMobil Technology and Engineering—Law Department (57) ABSTRACT

A method for deriving at least one pore or fluid relaxation parameter and endpoint selected from the group consisting of a longitudinal $T_1$ pore surface relaxivity constant ($\rho_1$), a transverse $T_2$ pore surface relaxivity constant ($\rho_2$), a pore surface-to-volume ratio (A/V), an equivalent pore-throat radius ($r_{eq}$), and a bulk fluid relaxation time ($T_B$) comprising: identifying modes in NMR $T_1$-$T_2$ data; assigning the modes to a poro-fluid class; clustering the modes based on poro-fluid class; estimating $T_B$ based on an asymptote fit of the clusters using $T_1$ and $T_2$ relaxation mechanisms in a bulk fluid relaxation-dominated limit; estimating $\rho_2/\rho_1$ based on an asymptote fit of the clusters using $T_1$ and $T_2$ relaxation mechanisms in a surface relaxation-dominated limit; fitting (Continued)

(l) Automatic 2D NMR Petrophysical Pore Multimodal Analysis (NPPM)

the $T_1$ and $T_2$ relaxation mechanisms to the clusters using the estimated $T_B$; and deriving the pore or fluid relaxation parameter and endpoint for the poro-fluid classes from the fit.

20 Claims, 7 Drawing Sheets

(51) Int. Cl.
*E21B 49/02* (2006.01)
*E21B 49/08* (2006.01)
*G01N 15/08* (2006.01)
*G01N 33/24* (2006.01)
*G01R 33/50* (2006.01)
*G01V 3/32* (2006.01)
*G01V 3/38* (2006.01)

(52) U.S. Cl.
CPC ....... *E21B 49/0875* (2020.05); *G01N 15/088* (2013.01); *G01N 24/081* (2013.01); *G01N 24/082* (2013.01); *G01N 33/241* (2013.01); *G01R 33/50* (2013.01); *G01V 3/32* (2013.01); *G01V 3/38* (2013.01); *G01N 2015/0846* (2013.01)

(58) Field of Classification Search
CPC ......... G01N 15/088; G01N 2015/0846; G01N 24/082; G01N 33/241; G01R 33/448; G01R 33/50; E21B 49/02; E21B 49/0875; E21B 49/088; E21B 7/046; E21B 47/053; E21B 47/11; E21B 47/111
See application file for complete search history.

(56) References Cited

OTHER PUBLICATIONS

Anand, V. et al. (2017) "Unlocking the Potential of Unconventional Reservoirs Through New Generation NMR T1/T2 Logging Measurements Integrated with Advanced Wireline Logs", Petrophysics, vol. 58, No. 2, pp. 81-96.

Brownstein, K. R. et al. (1979) "Importance of Classical Diffusion in NMR Studies of Water in Biological Cells", Physical Review A, vol. 19, No. 6, pp. 2446-2453.
Hirasaki, G. J. et al. (2003) "NMR Properties of Petroleum Reservoir Fluids", Magnetic Resonance Imaging, vol. 21, No. 3-4, pp. 269-277.
Ijasan, O. et al. (2020) "Estimating Characteristic Relaxation Properties from NMR T1-T2 Measurements in Unconventional Reservoirs", Unconventional Resources Technology Conference, Jul. 20-22, 2020 (URTEC-2020-3346-MS), pp. 1-18.
Kausik, R. et al. (2016) "NMR Relaxometry in Shale and Implications for Logging", Petrophysics, vol. 57, No. 4, pp. 339-350.
Kenyon, W. E. (1997) "Petrophysical Principles of Applications of NMR Logging", The Log Analyst, vol. 38, No. 2, pp. 21-43.
Nelson, P. H. (1994) "Permeability Porosity Relationships in Sedimentary Rocks", The Log Analyst, vol. 35, No. 3, pp. 38-62.
Venkataramanan, L. et al. (2018) "An Unsupervised Learning Algorithm to Compute Fluid Volumes from NMR T1-T2 Logs in Unconventional Reservoirs", Petrophysics, vol. 59, No. 5 (Oct. 2018), pp. 617-632; Originally presented as Transactions of the Society of Petrophysicists and Well Log Analysts, 59th Annual Logging Symposium, London, UK, Jun. 2-6, 2018, Paper Y.
Xie, H. et al. (2019) "Investigation of Physical Properties of Hydrocarbons in Unconventional Mudstones Using Two-Dimensional NMR Relaxometry", Transactions of the Society of Petrophysicists and Well Log Analysts, 60th Annual Logging Symposium, Jun. 15-19, 2019, pp. 1-10.
Ye, S. et al. (2019) "Method of Determining Unconventional Reservoir Saturation with NMR Logging", Society of Petroleum Engineers Annual Technical Conference and Exhibition, SPE-196069-MS, pp. 1-15.
Aster, R. C. et al. (2005a) "Tikhonov Regularization", Parameter Estimation and Inverse Problems, vol. 90, pp. 89-118.
Aster, R. C. et al. (2005b) "Nonlinear Regression", Parameter Estimation and Inverse Problems, vol. 90, pp. 171-199.
Hansen, P. C. (2010a) "Computational Aspects: Regularization Methods", Discrete Inverse Problems: Insights and Algorithms, Society of Industrial and Applied Mathematics, Monographs on Fundamentals of Algorithms, pp. 53-79.
Hansen, P. C. (2010b) "Getting Serious: Choosing the Regularization Parameter", Discrete Inverse Problems: Insights and Algorithms, Society of Industrial and Applied Mathematics, Monographs on Fundamentals of Algorithms, pp. 85-105.

\* cited by examiner

ESTIMATING PORE AND FLUID CHARACTERISTIC PROPERTIES IN ROCK SAMPLES USING NUCLEAR MAGNETIC RESONANCE ANALYSES

CROSS REFERENCE TO RELATED APPLICATIONS

This application claims the benefit of U.S. Provisional Application No. 62/930,275 filed Nov. 4, 2019 and U.S. Provisional Application No. 62/930,270 filed Nov. 4, 2019, the disclosures of which are incorporated herein by reference in their entirety.

BACKGROUND

The present disclosure relates to nuclear magnetic resonance (NMR) analyses for identifying the types of fluids and estimating associated pore and fluid characteristic properties in rock samples (e.g., a core sample from a subterranean formation and/or a portion of rock in the subterranean formation and/or a synthetic core sample) and/or borehole logging techniques.

During oil and gas exploration, zones with higher concentrations of oil and gas can be identified as target zones. One method of identifying target zones is using NMR analysis with core samples and/or logging techniques.

One such NMR technique is to analyze a two-dimensional NMR cross-plot, specifically of the longitudinal relaxation time ($T_1$) versus the transverse relaxation time ($T_2$). The sum of the NMR signal amplitude over the $T_1$-$T_2$ cross-plot is proportional to the total fluid-filled porosity of the sample for which the NMR measurements were performed. Because such data is typically analyzed independently sample-by-sample, there is limited integration across multiple data sets to provide additional information regarding the rock samples and fluids therein. That is, many important petrophysical parameters such as surface relaxivities, bulk fluid relaxation times, and pore size parameters are ignored, and potentially valuable information regarding the rock samples are never analyzed.

SUMMARY OF THE INVENTION

The present disclosure relates to NMR analyses for estimating pore and fluid characteristic properties, such as surface relaxivity constants, bulk fluid relaxation times, and pore surface-to-volume ratios used for calculating petrophysical properties (e.g., fluid viscosity, gas-oil ratio, and rock permeability).

A nonlimiting example method of the present disclosure comprises: identifying modes in NMR $T_1$-$T_2$ data from a plurality of samples; assigning the modes to a poro-fluid class; clustering the modes based on poro-fluid class to produce a plurality of clusters, wherein each cluster represents one or more poro-fluid classes; estimating a bulk fluid relaxation time (estimated $T_B$) based on an asymptote fit of the clusters, wherein the asymptote is based on $T_1$ and $T_2$ relaxation mechanisms in the bulk fluid relaxation-dominated limit; estimating a ratio of $\rho_2/\rho_1$ based on an asymptote fit of the clusters, wherein the asymptote is based on $T_1$ and $T_2$ relaxation mechanisms in the surface relaxation-dominated limit; fitting the $T_1$ relaxation mechanisms and the $T_2$ relaxation mechanisms to one or more of the clusters using the estimated $T_B$; and deriving at least one pore or fluid relaxation parameter and endpoint for the poro-fluid classes from the fit, wherein the at least one pore or fluid relaxation parameter and endpoint is selected from the group consisting of a longitudinal $T_1$ pore surface relaxivity constant ($\rho_1$), a transverse $T_2$ pore surface relaxivity constant ($\rho_2$), a pore surface-to-volume ratio (A/V), an equivalent pore-throat radius ($r_{eq}$), and a bulk fluid relaxation time ($T_B$).

A nonlimiting example computing device of the present disclosure comprises: a processor; a memory coupled to the processor; and instructions provided to the memory, wherein the instructions are executable by the processor to perform the method according to any of the foregoing nonlimiting example method embodiments.

BRIEF DESCRIPTION OF THE DRAWINGS

The following figures are included to illustrate certain aspects of the embodiments, and should not be viewed as exclusive embodiments. The subject matter disclosed is capable of considerable modifications, alterations, combinations, and equivalents in form and function, as will occur to those skilled in the art and having the benefit of this disclosure.

FIG. 2(H) is the fractional saturation or relative percentages of modal pore volumes with respect to total fluid-filled volume.

DETAILED DESCRIPTION

The present disclosure relates to NMR analyses for deriving pore and fluid relaxation parameters or endpoints including pore surface relaxivity constants (which are related to rock mineralogy, wettability, and controlled by pore fluid-to-grain surface relaxation interactions), bulk fluid relaxation times (which are related to fluid viscosity, gas-oil ratio, and controlled by fluid hydrogen proton density), and pore size surface-to-volume ratios (which are related to pore dimension, pore-throat sizes and, consequently, rock permeability). As a result of the NMR analyses described herein, a greater understanding of what fluid compositions and volumes are in what types of pore structures can be achieved for further prediction of rock and fluid characteristic properties such as permeability and fluid viscosity, and classification of reservoir rock quality. From such information, an operator can determine, for example, which fluids are accessible in which parts of a subterranean formation and if stimulation operations should be performed to more readily access said fluids.

First, modes (or peaks) in the NMR $T_1$-$T_2$ data (e.g., $T_1$-$T_2$ cross-plots and other plots) of fluid in several rock samples (e.g., a core sample from a subterranean formation and/or a portion of rock in the subterranean formation and/or a synthetic core sample) are identified. Then, modes are assigned to a fluid type that may be in a specific pore-size (referred to herein as poro-fluid class). Then, clusters of modes are identified based on the poro-fluid class of the modes where a cluster may represent one or more poro-fluid classes. The identification of modes and assignment of poro-fluid class for each mode can be performed by any of several methods.

The NMR $T_1$-$T_2$ data is used generically to describe a plot or mathematical representation thereof (e.g., table, series of mathematical equations, or the like) of a measure of the NMR signal amplitude (e.g., A or any mathematical manipulation of A) as a function of a measure of $T_1$ (e.g., absolute value of $T_1$, $\log_{10} T_1$, or any other mathematical manipulation of $T_1$) and/or a measure of $T_2$ (e.g., absolute value of $T_2$, $\log_{10} T_2$, or any other mathematical manipulation of $T_2$). The NMR $T_1$-$T_2$ data can be analyzed, for example, as a 2-dimensional or a 3-dimensional plot. 2-dimensional plots typically have the measure of $T_1$ and the measure of $T_2$ are the y- and x-axes (in either configuration) and the measure of amplitude represented with contours or colors, for example, in the 2-dimensional space. NMR $T_1$-$T_2$ data may also be a plot of the ratio of $T_1/T_2$ as a function of $T_1$ and/or a plot of the ratio of $T_1/T_2$ as a function of $T_2$ where in each plot the measure of amplitude is represented with contours or colors, for example, in the 2-dimensional space. Other plots and plot representations described herein are similarly a plot or mathematical representation thereof.

The NMR $T_1$-$T_2$ data is first analyzed to identify modes in the NMR $T_1$-$T_2$ data. For example, a peak amplitude threshold value (e.g., absolute value, minimum percentage of peak amplitude of the $T_1$-$T_2$ cross-plot, and the like) can be used to automatically define the presence or absence of a mode in a local maxima and inflections. Alternatively, the modes can be visually or manually identified by the user. A user can determine a desired level of granularity when defining modes and subsequently assigning modes to poro-fluid classes. For example, two modes may overlap and the user may opt to identify the two overlapping modes as one poro-fluid class or two poro-fluid classes.

When modes are identified mathematically, deconvolution or decomposition can be used in analyzing the NMR $T_1$-$T_2$ data for the identification of modes. For example, the modes of the $T_1$-$T_2$ cross-plots can be deconvolved using any variety of peak shape basis functions. Examples of peak shape basis functions include, but are not limited to, Gaussian, Lorentzian, Voigt, exponentially modified Gaussian, and the like, and any variation thereof. A preferred peak shape basis function is Gaussian because it tends to better describe geologic processes and produce better conformed peak shape basic functions.

It should be noted that because NMR $T_1$-$T_2$ data from several samples are analyzed, each sample may have a different number of modes. For example, a mode that is present in a first sample may not be present in a second sample because the poro-fluid that contributes to said mode is not present in the second sample.

The modes identified in several samples are then segregated into clusters of modes based on the poro-fluid class of the modes. A single cluster may represent one or more poro-fluid classes.

Examples of poro-fluid classes include, but are not limited to, free fluid, fluid in pores, fluid in macroporosity or fractures, fluid in inorganic pores, fluid in organic pores, free liquid, liquid in pores, liquid in macroporosity or fractures, liquid in inorganic pores, liquid in organic pores, free gas, gas in pores, gas in macroporosity or fractures, gas in inorganic pores, gas in organic pores, free oil, oil in pores, oil in macroporosity or fractures, oil in inorganic pores, oil in organic pores, free water, water in pores, water in macroporosity or fractures, water in inorganic pores, water in organic pores, clay-associated water, clay-bound water, surface relaxation-dominated fluid, surface relaxation-dominated oil, surface relaxation-dominated water, bulk relaxation-dominated fluid, bulk relaxation-dominated oil, bulk relaxation-dominated water, bulk relaxation-dominated gas, bound fluid, bound oil, bound water, capillary-bound fluid, capillary-bound water, capillary-bound oil, bitumen, free hydrocarbon, bound hydrocarbon, and the like, and any combination thereof. Again, not every sample may have a poro-fluid class, so a sample may have fewer modes than the number of poro-fluid classes in the cumulative NMR $T_1$-$T_2$ data from several samples.

Again, the desired level of granularity can be applied when identifying which modes belong to which poro-fluid class, the number of poro-fluid classes considered, and the number of clusters considered. For example, a user can decide that only 5 poro-fluid classes (e.g., free oil, free water, oil in pores, water in pores, and other fluids) are of interest. Accordingly, if the NMR $T_1$-$T_2$ data has more than 5 modes, more than one mode (overlapping or not) may be assigned to a single poro-fluid class. In yet another example, a cluster can represent oil in general and comprise modes identified as free oil, oil in pores, oil in macroporosity or fractures, oil in inorganic pores, and oil in organic pores. Alternatively, a first cluster can represent free oil and a second cluster can represent oil in pores (e.g., comprising oil in macroporosity or fractures, oil in inorganic pores, oil in organic pores, and the like).

Clustering of the modes can be performed by any suitable method. For example, a user can define the poro-fluid class for each mode. Alternatively or additionally, partitioning methods may be used to assign a poro-fluid class to each mode. Generally, in partitioning methods a set of established criteria define the boundaries of a classification. In this instance, criteria related to the NMR $T_1$-$T_2$ data may define individual poro-fluid classes. Without limitation, the $T_1/T_2$ ratio may relate to the fluid type (e.g., oil, water, gas, and the like), the $T_2$ relaxation time may relate to the pore size and mobility of the fluid, and the $T_1$ relaxation time may relate to fluid type, rock wettability, or NMR activation sequence. Therefore, each may be analyzed individually or in comparison to each other to assign each mode to a poro-fluid class. For example, a cross-plot of a measure of $T_1$ and a measure of $T_2$ may have a plurality of regions identified therein where when a mode falls within a region the mode is considered to be a specific poro-fluid class. Alternatively, mathematical relationships between $T_1$ and $T_2$ can be used to define different poro-fluid classes. One skilled in the art will recognize various partitioning methods that can be used. Another nonlimiting example of partitioning is provided in the Examples section herein.

When mathematically identifying clusters, the cluster analysis can be performed, for example, with partitioning algorithms, hierarch algorithms, density-based algorithms, grid-based algorithms, graph-based algorithms, and the like, and any combination thereof. One skilled in the art without undo experimentation will recognize how to identify a poro-fluid class based on values of means, weighted-means, or moments of poro-fluid modal properties within the same cluster.

Once the clusters have been identified, the pore and fluid relaxation parameters or endpoints of the poro-fluid classes can be derived by analyzing each of the clusters. As described above, any level of granularity can be analyzed. In some instances, while several clusters may be mathematically analyzed and/or identified in the first part, some of said clusters may then be collectively combined into a single composite cluster. For example, oil inside small pores and oil inside large pores identified as separate clusters by the mathematical analysis may be grouped together for additional analysis. The level of granularity of the analysis of the complete methods described herein has more than one location at which the analysis can become broader and less granular, if desired.

In the second portion of the methods and systems described herein, a calibration or regression fit to the principles that describe the physics of $T_1$ and $T_2$ relaxation mechanisms can be applied to the desired clusters. Said $T_1$ and $T_2$ relaxation mechanisms are controlled by rock pore parameters (also referred to herein as pore and fluid relaxation parameters or endpoints) that include (a) pore surface relaxivity constants ($\rho_1$ for $T_1$ and $\rho_2$ for $T_2$), which relate to rock mineralogy, wettability, and controlled by pore fluid-to-grain surface interactions; (b) bulk fluid relaxation times ($T_{1B}$ for $T_1$ and $T_{2B}$ for $T_2$), which relate to the fluid viscosity and hydrogen proton density; and (c) the pore size surface-to-volume ratios, which relate to pore dimension, pore-throat radii, and rock permeability.

More specifically, for a pore saturated with wetting and non-wetting fluids, Eqs. 1 and 2 are the $T_2$ and $T_1$ relaxation mechanisms, respectively, describing apparent relaxation rates of a given fluid f (see Brownstein, K. R., and Tarr, C. E., 1979, Importance of classical diffusion in NMR studies of water in biological cells: Physical Review A, volume 19, no. 6, 2446-2453; and Kenyon, W. E., 1997, Petrophysical principles of applications of NMR logging: The Log Analyst, 38, no. 2, 21-43).

$$\frac{1}{T_{2,f}} = \frac{1}{T_{2B,f}} + \frac{\rho_{2,f}}{S_f}\left(\frac{A}{V}\right)_f + \frac{D_f(\gamma G T_e)^2}{12} \qquad \text{Eq. 1}$$

$$\frac{1}{T_{1,f}} = \frac{1}{T_{1B,f}} + \frac{\rho_{1,f}}{S_f}\left(\frac{A}{V}\right)_f \qquad \text{Eq. 2}$$

where subscript f represents fluid type of the cluster (e.g., a specific poro-fluid type or a combination of poro-fluid types that, for example, correspond to water, oil, gas, or the like), $S_f$ is the relative volume fraction of fluid type of the cluster f to the total pore fluid-filled space $\phi_t$, $T_{2B}$ and $T_{1B}$ are transverse and longitudinal bulk fluid relaxation times in seconds, respectively; $\rho_2$ and $\rho_1$ are transverse and longitudinal pore surface relaxivity constants in μm/s, respectively; A is pore surface area in μm²; V is pore volume in μm³; D is molecular diffusion coefficient in cm²/s; γ is proton gyromagnetic ratio in MHz/Tesla; G is field-strength gradient in G/cm; and $T_e$ is inter-echo spacing used in the CPMG (Car-Purcell-Meiboom-Gill) sequence in seconds. Due to minimal internal gradients and low $T_e$ in most $T_1$ and $T_2$ data acquisitions, the diffusion term (third term on right-hand side of Eq. 1) is negligible. Also, for most reservoir fluids, $T_{2B} \approx T_{1b} \approx T_B$.

In surface relaxation-dominated limit, i.e., very small nano- to micro-pore sizes with very low $T_2$s, relaxation due to fluid interactions with pore wall surfaces dominate the NMR response such that the surface relaxation term, i.e., second term on the right-hand side of Eqs. 1-2 dominates the relaxation rates and controls the total apparent relaxation. Hence the apparent $T_1/T_2$ ratio, for a given fluid, approaches a constant value of $\rho_2/\rho_1$. As pore size and $T_2$ increase, effect of surface relaxation term decreases and bulk fluid relaxation term, i.e., first term on the right-hand side of Eqs. 1-2, competes with the surface relaxation rate. In the bulk fluid relaxation-dominated limit, i.e., larger macro-pores and fractures, the unconfined fluid relaxation rate dominates the apparent relaxation response, $T_1/T_2$ ratio approaches unity, and the $T_1/T_2$ ratio is independent of fluid type. In this limit, $T_B$ can be initially estimated based on the value of $T_2$ or $T_1$ at the asymptote of the poro-fluid modes as $T_1/T_2$ ratio approached unity in the $T_1/T_2$ ratio as a function of $T_2$ or $T_1$ plots. This is a reasonable initial approximation of $T_B$. On the other hand, relaxation interactions in organic matter (OM) pores are significantly dominated by homonuclear dipolar coupling such that the bulk fluid relaxation-dominated limit is not apparent and total relaxation can be effectively modeled with only the second term in the right-hand side of Eqs. 1-2. In the continuum, Eqs. 1 and 2 are re-parameterized as Eq. 3, i.e., $$\log_{10}(T_{ns,f}/S_f) = -\log_{10}\rho_{n,f} - \log_{10}\left(\frac{A}{V}\right)_f \qquad \text{Eq. 3}$$

where $$\frac{1}{T_{ns,f}} = \frac{1}{T_{n,f}} - \frac{1}{T_{B,f}} = \frac{\rho_{n,f}}{S_f}\left(\frac{A}{V}\right)_f,$$

and $T_{ns}$ is surface relaxation time of n=1 and 2 for longitudinal and transverse relaxation, respectively.

Then, a system of equations, based on Eq. 3, can be used to define empirical calibration of the relaxation mechanisms. For example, Eq. 4 is an illustrative example of said system of equations.

$$\min\left\|\begin{bmatrix} -1 & 0 & & \\ \vdots & & -I_{N_d} & \\ -1 & 0 & & \\ 0 & -1 & & \\ \vdots & & -I_{N_d} & \\ 0 & -1 & & \end{bmatrix} \begin{bmatrix} \log_{10}\rho_{2,f} \\ \log_{10}\rho_{1,f} \\ \log_{10}(A/V)_{f,1} \\ \vdots \\ \log_{10}(A/V)_{f,N_d} \end{bmatrix} - \begin{bmatrix} \log_{10}(T_{2s,f}/S_f)_1 \\ \vdots \\ \log_{10}(T_{2s,f}/S_f)_{N_d} \\ \log_{10}(T_{1s,f}/S_f)_1 \\ \vdots \\ \log_{10}(T_{1s,f}/S_f)_{N_d} \end{bmatrix} W_d \right\|_2^2 \qquad \text{Eq. 4}$$

where $N_d$ is the total number of modes (peaks) of clustered fluid type f; $I_{Nd}$ is $N_d \times N_d$ identity matrix; $W_d$ is the data-weighting matrix per Eq. 5; and the second matrix is the unknown model matrix of pore relaxation parameters to be solved.

$$W_d = \begin{bmatrix} \phi_{if,1} \\ \vdots \\ \phi_{if,N_d} \\ \phi_{if,1} \\ \vdots \\ \phi_{if,N_d} \end{bmatrix}^c \quad \text{Eq. 5}$$

where $\phi_{if}$ is the fractional pore volume for mode i with a certain clustered fluid type f of which $S_f = \phi_{if}/\phi_t$; and c is a real number.

In this example, the data-weighting matrix is proportional to the fractional pore volume of each mode in the system of equations such that higher pore volumes may dominate the calibration.

Alternative to Eq. 5, $W_d$ can be used as an importance matrix for prioritizing data quality, signal-to-noise, or any conditioning of the calibration to a more realistic or physically meaningful result.

The solution to Eqs. 3-5, per clustered fluid type, gives the pore and fluid relaxation parameters or endpoints critical for fluid and reservoir quality determination. These parameters are (a) pore surface relaxivity constants, $\rho_{2f}$ and $\rho_{1f}$, (b) bulk fluid relaxation times, $T_{Bf}$, and (c) pore surface-to-volume ratio, $(A/V)_f$, each described above. A/V ratio is 3/r when assuming spherical pores and 2/r for cylindrical pores, where r is pore radius in μm, i.e., generally it can be parameterized as $A/V = m_g/r_{eq}$, where $m_g$ is a geometrical factor and $r_{eq}$ is equivalent pore-throat parameter in μm. It is critical to emphasize that because the calibration is implemented per clustered fluid type f, the parameters are obtained for each clustered fluid as implemented in the cluster associations, i.e., delineating oil-saturated, water-saturated, organic matter pores, or/and gas-saturated pore sizes in the porous media.

As described above, $T_B$ is initially estimated in the bulk fluid relaxation-dominated limit based on the value of $T_2$ or $T_1$ at the asymptote of the poro-fluid modes as $T_1/T_2$ ratio approached unity using the data in the $T_1/T_2$ ratio as a function of $T_2$ and $T_1$ plot. Once the pore and fluid relaxation parameters are derived, the $T_B$ can be iteratively adjusted per clustered fluid, to improve and optimize the calibration (Eqs. 3-5) and, consequently, updated pore and fluid relaxation endpoints are iteratively derived to a best fit or fit within a desired threshold of error.

With these pore and fluid relaxation endpoints, pore surface-to-volume ratio can then, and for newly acquired data, be approximated using Eq. 6.

$$\Sigma_{p,f} \equiv \frac{m_g}{r_{eq,f}} = \left(\frac{A}{V}\right)_f \approx \frac{\frac{1}{T_{2,f}} + \frac{1}{T_{1,f}} - \frac{2}{T_{B,f}}}{\rho_{2,f} + \rho_{1,f}} S_f. \quad \text{Eq. 6}$$

Newly acquired data can then be analyzed to derive the pore size-to-volume ratios or pore-throat radii that each clustered fluid occupies in the porous media. Hydrocarbon viscosity can then be calculated using $T_{B,f}$ correlations to viscosity as described by Hirasaki, G. J., Lo, S., and Zhang, Y., 2003, NMR properties of petroleum reservoir fluids: Magnetic Resonance Imaging, 21, no. 3-4, 269-277. Rock permeability or relative permeability can also be calculated using $\Sigma_{p,f}$ correlations to permeability and flow potential as described by Nelson, P. H., 1994, Permeability-porosity relationships in sedimentary rocks: The Log Analyst, 35, no. 3, 38-62.

Figure 1:
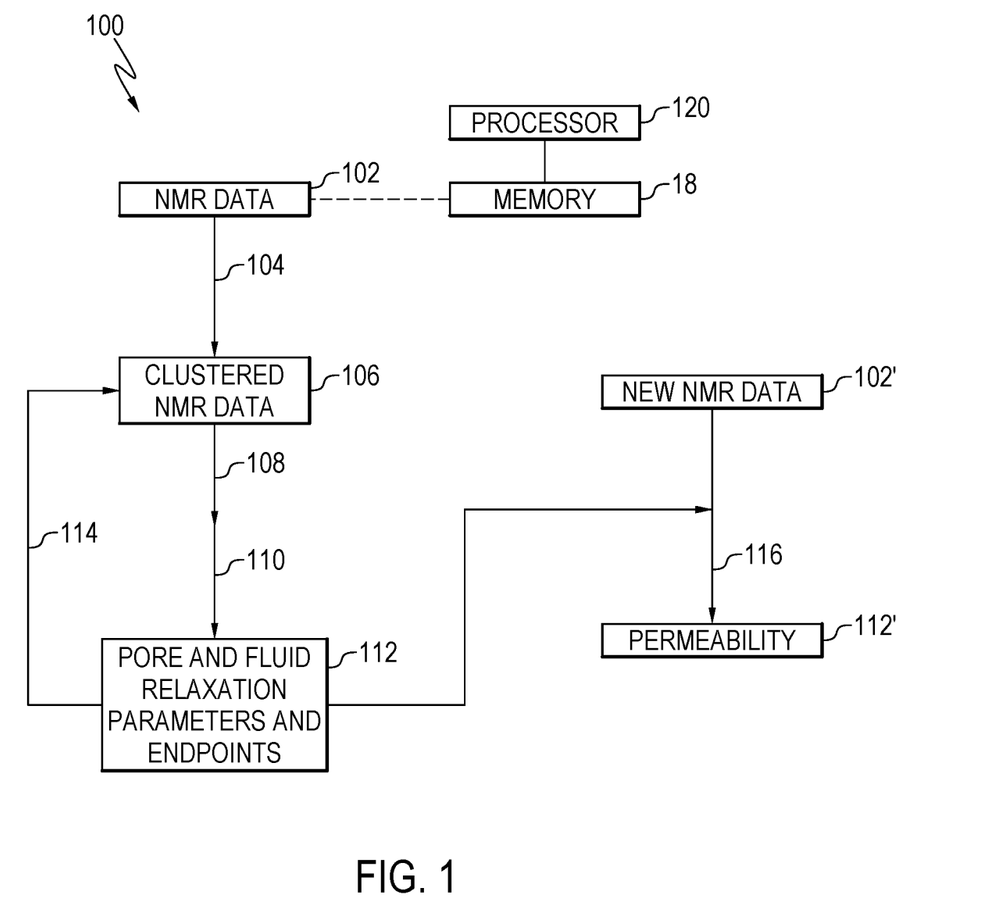
FIG. 1 is a diagram of a nonlimiting example computer system and method of the present disclosure.

FIG. 1 is a diagram of a nonlimiting example computer system and method 100 of the present disclosure. First, NMR $T_1$-$T_2$ data 102 is collected in a plurality of rock samples (e.g., a core sample from a subterranean formation and/or a portion of rock in the subterranean formation and/or a synthetic core sample). An analysis 104 is performed on the NMR data 102 where the modes in the NMR data 102 are determined and assigned to poro-fluid classes and then modes of each cluster are considered as a cluster of data points. The result of the analysis is clustered NMR data 106 that may represent a fluid type that may be in pores of varying sizes (e.g., a specific poro-fluid type or a combination of poro-fluid types that, for example, correspond generally to water, oil, gas, or the like optionally with further differentiation of in or out of pores). The clustered NMR data 106 may be represented by plots, table, or other mathematical representations of the data. An initial $T_B$ for a cluster is then estimated 108 from the clustered NMR data 106 as described above. Using the initial $T_B$, the clustered NMR data 106 are mathematically fit 110 to the pore relaxation mechanism equations to solve for the pore and fluid relaxation parameters and endpoints 112 for each of the clusters. Then, the process of estimating $T_B$ and mathematically fitting 110 the clustered NMR data 106 to the pore relaxation mechanism equations is iteratively 114 performed until best fit or fit within a desired threshold of error is achieved in the pore and fluid relaxation endpoints 112. Final $T_B$ can be correlated to fluid viscosity 112, final A/V can be used to calculate permeability 112, and final $\rho_2$ and $\rho_1$ can be used to infer rock mineralogy and wettability. Instructions to cause a processor 120 to perform the method 100 may be stored on a memory 118.

Then, newly acquired NMR data 102' can be analyzed 116 using the pore and fluid relaxation parameters and endpoints 112 and their relationship to $T_1$, $T_2$, poro-fluid class, or any combination thereof to determine the pore relaxation parameters, and consequently reservoir quality metrics including permeability, 112' for the modes of the newly acquired NMR data 102'.

Various aspects of the systems and methods described herein utilize computer systems. Such systems and methods can include a non-transitory computer readable medium containing instructions that, when implemented, cause one or more processors to carry out the methods described herein.

"Computer-readable medium" or "non-transitory, computer-readable medium," as used herein, refers to any non-transitory storage and/or transmission medium that participates in providing instructions to a processor for execution. Such a medium may include, but is not limited to, non-volatile media and volatile media. Non-volatile media includes, for example, NVRAM, or magnetic or optical disks. Volatile media includes dynamic memory, such as main memory. Common forms of computer-readable media include, for example, a floppy disk, a flexible disk, a hard disk, an array of hard disks, a magnetic tape, or any other magnetic medium, magneto-optical medium, a CD-ROM, a holographic medium, any other optical medium, a RAM, a PROM, and EPROM, a FLASH-EPROM, a solid state medium like a memory card, any other memory chip or cartridge, or any other tangible medium from which a computer can read data or instructions. When the computer-readable media is configured as a database, it is to be understood that the database may be any type of database, such as relational, hierarchical, object-oriented, and/or the like. Accordingly, exemplary embodiments of the present systems and methods may be considered to include a tangible storage medium or tangible distribution medium and prior art-recognized equivalents and successor media, in which the software implementations embodying the present techniques are stored.

The methods described herein can, and in many embodiments must, be performed using computing devices or processor-based devices that include a processor; a memory coupled to the processor; and instructions provided to the memory, wherein the instructions are executable by the processor to perform the methods described herein (such computing or processor-based devices may be referred to generally by the shorthand "computer"). For example, any one or more of the following may be carried out using a computer: identifying modes in NMR $T_1$-$T_2$ data may be carried out using a computer (although this may also be carried out manually, e.g., by observation); assigning modes to a poro-fluid class; clustering the modes (e.g., based on poro-fluid class) to produce a plurality of clusters; estimating bulk fluid relaxation time ($T_B$); estimating a ratio of $\rho_2/\rho_1$; fitting $T_1$ relaxation mechanisms and $T_2$ relaxation mechanisms to one or more of the clusters (e.g., using estimated $T_B$); and/or deriving at least one pore or fluid relaxation parameter and endpoint for the poro-fluid classes from the aforementioned fit. Similarly, any calculation, determination, or analysis recited as part of methods described herein will in may embodiments be carried out in whole or in part using a computer.

Furthermore, the instructions of such computing devices or processor-based devices can be a portion of code on a non-transitory computer readable medium. Any suitable processor-based device may be utilized for implementing all or a portion of embodiments of the present techniques, including without limitation personal computers, networks personal computers, laptop computers, computer workstations, mobile devices, multi-processor servers or workstations with (or without) shared memory, high performance computers, and the like. Moreover, embodiments may be implemented on application specific integrated circuits (ASICs) or very large scale integrated (VLSI) circuits.

The presently-described methods may all be deployed in managing hydrocarbons in the subterranean formation. As used herein, "managing hydrocarbons" or "hydrocarbon management" includes any one or more of the following: hydrocarbon extraction; hydrocarbon production, (e.g., drilling a well and prospecting for, and/or producing, hydrocarbons using the well; and/or, causing a well to be drilled, e.g., to prospect for hydrocarbons); hydrocarbon exploration; identifying potential hydrocarbon systems such as those including hydrocarbon-bearing formations; determining candidate-sampling locations within a hydrocarbon system; evaluating a hydrocarbon system; characterizing a hydrocarbon system such as a hydrocarbon-bearing formation; identifying well locations; determining well injection rates; determining well extraction rates; identifying reservoir connectivity; acquiring, disposing of, and/or abandoning hydrocarbon resources; reviewing prior hydrocarbon management decisions; and any other hydrocarbon-related acts or activities, such activities typically taking place with respect to a hydrocarbon system and/or subsurface formation. In particular embodiments, managing hydrocarbons may include one or more of identifying a zone of the subsurface formation for completion, and carrying out one or more completion operations on or in the identified zone; identifying a portion of the subterranean formation from where to obtain a core sample for further analysis, and obtaining one or more core samples from the identified portion; carrying out a simulation or completion operation on the subterranean formation; and/or identifying a horizontal well landing location within the subterranean formation and causing a horizontal well to be drilled to the identified landing location. The aforementioned broadly include not only the acts themselves (e.g., extraction, production, drilling a well, etc.), but also or instead the direction and/or causation of such acts (e.g., causing hydrocarbons to be extracted, causing hydrocarbons to be produced, causing a well to be drilled, causing the prospecting of hydrocarbons, etc.). Furthermore, methods may in particular include managing hydrocarbons based at least in part upon a determined relative concentration, abundance, and/or net NMR signal amplitude corresponding to clusters as a function of pore size surface-to-volume ratio (A/V) or pore-throat radius ($r_{eq}$). Or, in other embodiments, managing hydrocarbons may be carried out based at least in part upon calculated fluid viscosity or gas-oil ratio (based on $T_B$), rock permeability (calculated based upon A/V or $r_{eq}$), and/or rock mineralogy and wettability (calculated based on $\rho_2$ and $\rho_1$) for each cluster.

Example Embodiments

A nonlimiting example embodiment of the present disclosure is a method comprising: identifying modes in NMR $T_1$-$T_2$ data from a plurality of samples; assigning the modes to a poro-fluid class; clustering the modes based on poro-fluid class to produce a plurality of clusters, wherein each cluster represents one or more poro-fluid classes; estimating a bulk fluid relaxation time (estimated $T_B$) based on an asymptote fit of the clusters, wherein the asymptote is based on $T_1$ and $T_2$ relaxation mechanisms in the bulk fluid relaxation-dominated limit; estimating a ratio of $\rho_2/\rho_1$ based on an asymptote fit of the clusters, wherein the asymptote is based on $T_1$ and $T_2$ relaxation mechanisms in the surface relaxation-dominated limit; fitting the $T_1$ relaxation mechanisms and the $T_2$ relaxation mechanisms to one or more of the clusters using the estimated $T_B$; and deriving at least one pore or fluid relaxation parameter and endpoint for the poro-fluid classes from the fit, wherein the at least one pore or fluid relaxation parameter and endpoint is selected from the group consisting of a longitudinal $T_1$ pore surface relaxivity constant ($\rho_1$), a transverse $T_2$ pore surface relaxivity constant ($\rho_2$), a pore surface-to-volume ratio (A/V), an equivalent pore-throat radius ($r_{eq}$), and a bulk fluid relaxation time ($T_B$). Said example method embodiment may further include one or more of the following: Element 1: the method further comprising: iteratively (a) calculating the $T_B$ and (b) deriving the fit, wherein the at least one pore or fluid relaxation parameter is based on one of the iteratively derived fits; Element 2: the method further comprising: determining a relative concentration, abundance, and/or net NMR signal amplitude corresponding to clusters as a function of pore size surface-to-volume ratio (A/V) or pore-throat radius ($r_{eq}$); Element 3: the method further comprising: analyzing a newly acquired NMR $T_1$-$T_2$ data for a relative concentration, abundance, or net NMR signal amplitude of the clusters as a function of pore size surface-to-volume ratio (A/V) or pore throat radius ($r_{eq}$); Element 4: the method further comprising: calculating a fluid viscosity or gas-oil ratio for each cluster based on the $T_B$; calculating rock permeability for each cluster based on the pore size surface-to-volume ratio (A/V) or pore-throat radius ($r_{eq}$); and determining rock mineralogy and wettability for each cluster based on the longitudinal $T_1$ pore surface relaxivity constant ($\rho_1$) and transverse $T_2$ pore surface relaxivity constant ($\rho_2$); Element 5: one or more of Elements 2-4 and wherein the rock sample is a subterranean formation or a core sample from the subterranean formation, and the method further comprises: identifying a zone of the subterranean formation for completion; Element 6: one or more of Elements 2-4 and wherein the rock sample is a subterranean formation or a core sample from the subterranean formation, and the method further comprises: identifying a portion of the subterranean formation from where to obtain a core sample for further analysis; Element 7: one or more of Elements 2-4 and wherein the rock sample is a subterranean formation or a core sample from the subterranean formation, and the method further comprises: determining a stimulation or completion operation to be performed on the subterranean formation; Element 8: one or more of Elements 2-4 and wherein the rock sample is a subterranean formation or a core sample from the subterranean formation, and the method further comprises: identifying a horizontal well landing location within the subterranean formation; Element 9: wherein clustering the modes for each poro-fluid class comprises: identifying modes in the NMR $T_1$-$T_2$ data with a multimodal deconvolution or decomposition with regularized nonlinear inversion; deriving a modal properties vector comprising modal properties for each of the modes; performing a cluster analysis of the modes to identify clusters; and assigning the poro-fluid class to the clusters based on one or more of the modal properties of the modes in each of the clusters; Element 10: Element 9 and wherein the multimodal deconvolution or decomposition is selected from the group consisting of Gaussian, Lorentzian, Voigt, exponentially modified Gaussian, and any variation thereof; Element 11: Element 9 and wherein the regularized nonlinear inversion is selected from the group consisting of Gauss-Newton inversion, Landweber inversion, Levenberg-Marquartz inversion, Occam's inversion, and any variation thereof; Element 12: Element 9 and wherein the nonlinear regularization inversion is an iterative calculation of multiple regularizations where the regularization in each iteration having a minimum misfit proceeds to the next iteration; Element 13: the method further comprising: wherein clustering the modes for each poro-fluid class comprises: identifying modes in the NMR $T_1$-$T_2$ data by manual analysis or visual inspection; Element 14: wherein the poro-fluid classes are selected from the group consisting of free fluid, fluid in pores, fluid in macroporosity or fractures, fluid in inorganic pores, fluid in organic pores, free liquid, liquid in pores, liquid in macroporosity or fractures, liquid in inorganic pores, liquid in organic pores, free gas, gas in pores, gas in macroporosity or fractures, gas in inorganic pores, gas in organic pores, free oil, oil in pores, oil in macroporosity or fractures, oil in inorganic pores, oil in organic pores, free water, water in pores, water in macroporosity or fractures, water in inorganic pores, water in organic pores, clay-associated water, clay-bound water, surface relaxation-dominated fluid, surface relaxation-dominated oil, surface relaxation-dominated water, bulk relaxation-dominated fluid, bulk relaxation-dominated oil, bulk relaxation-dominated water, bulk relaxation-dominated gas, bound fluid, bound oil, bound water, capillary-bound fluid, capillary-bound water, capillary-bound oil, bitumen and any combination thereof; Element 15: the method further comprising: wherein the NMR $T_1$-$T_2$ data is for fluids in a plurality of core samples from a subterranean formation; Element 16: wherein the NMR $T_1$-$T_2$ is from NMR logging data for fluids in a subterranean formation; Element 17: wherein the NMR $T_1$-$T_2$ is for fluids in a synthetic core sample; Element 18: the method further comprising: performing an NMR logging operation for a subterranean formation; deriving the at least one pore and fluid relaxation parameter for the poro-fluid classes from a first portion of the NMR logging operation in real-time; and analyzing a newly acquired NMR $T_1$-$T_2$ data for a second portion of the NMR logging operation based on the at least one pore and fluid relaxation parameter for the poro-fluid classes.

Another nonlimiting example embodiment is a computing device comprising: a processor; a memory coupled to the processor; and instructions provided to the memory, wherein the instructions are executable by the processor to perform the method according to any of the foregoing nonlimiting example method embodiments.

Examples of combinations of elements for the method embodiments and/or the computing device embodiments include, but are not limited to, two or more of Elements 1-8 in combination; two or more of Elements 5-8 in combination with one or more of Elements 1-4; two or more of Elements 9-12 in combination; one or more of Elements 1-8 in combination with Element 9 and optionally in further combination with one or more of Elements 10-12; Element 13 in combination with one or more of Elements 1-8; and one of Elements 15-19 in combination with one or more of Elements 1, 2, 3, 9, 10, 11, 12, 13, and 14.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present invention. At the very least, and not as an attempt to limit the application of the doctrine of equivalents to the scope of the claim, each numerical parameter should at least be construed in light of the number of reported significant digits and by applying ordinary rounding techniques.

One or more illustrative embodiments incorporating the invention embodiments disclosed herein are presented herein. Not all features of a physical implementation are described or shown in this application for the sake of clarity. It is understood that in the development of a physical embodiment incorporating the embodiments of the present invention, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill in the art and having benefit of this disclosure.

While compositions and methods are described herein in terms of "comprising" various components or steps, the compositions and methods can also "consist essentially of" or "consist of" the various components and steps.

To facilitate a better understanding of the embodiments of the present invention, the following examples of preferred or representative embodiments are given. In no way should the following examples be read to limit, or to define, the scope of the invention.

EXAMPLES

In a first part of the examples section, a nonlimiting example of identifying modes and poro-fluid classes is presented. This example describes a mathematical approach for NMR petrophysical pore multimodal (NPPM) analysis.

Figure 2A:
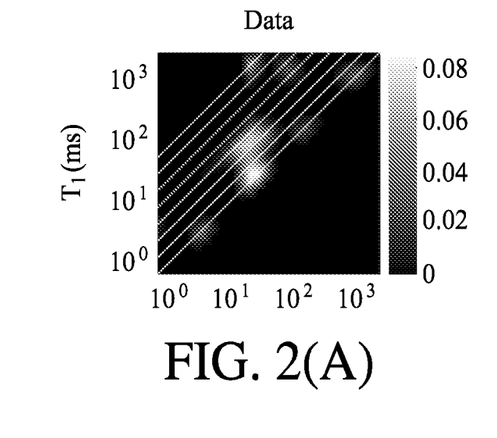
FIG. 2(A) is a data $T_1$-$T_2$ cross-plot.

FIG. 2(A) is a $T_1$-$T_2$ cross-plot of NMR data collected from a subterranean rock or core sample. The diagonal lines are generic lines that correspond to specific absolute values of $T_1/T_2$ ratios.

The $T_1$-$T_2$ cross-plot was deconvolved using multimodal Gaussian deconvolution or decomposition achieved with a regularized nonlinear Levenberg-Marquartz inversion. The 2D Gaussian mixture of multimodal poro-fluids representation is $$G_{t,2D} = \Sigma_i{}^I A_i \exp(-\tfrac{1}{2} x_i{}^T \sigma_i{}^{-1} x_i) \qquad \text{(Eq. 7)}$$

where $A_i$ is the peak poro-amplitude $$x_i = \begin{bmatrix} x_1 - \mu_{i1} \\ x_2 - \mu_{i2} \end{bmatrix}$$

where $x_1$ and $x_2$ are a logarithm of $T_1$ and $T_2$ relaxations, $\mu_{i1}$ and $\mu_{i2}$ are Gaussian mean centers in logarithm of $T_1$ and $T_2$ dimensions, respectively; superscript T represents matrix transpose notation;

$$\sigma_i = \begin{bmatrix} \sigma_{i1,1}^2 & \sigma_{i1,2}^2 \\ \sigma_{i2,1}^2 & \sigma_{i2,2}^2 \end{bmatrix}$$

is the shape covariance matrix which must be symmetric and positive definite; and subscript i represents the i-th Gaussian poro-fluid mode for which i=1, 2, . . . , I. In this example I=9 from automatic local maxima and inflections identification.

It follows, in a Gaussian representation, that fractional pore volume, $\phi_i$, associated with mode i is given as $$\phi_i = A_i \sqrt{\frac{4\pi^2}{|\sigma_i^{-1}|}} \qquad \text{(Eq. 8)}$$

where total fluid-filled NMR porosity, $\phi_t$, is $$\phi_t = \Sigma_i{}^I \phi_i. \qquad \text{(Eq. 9)}$$

Therefore, the multimodal poro-fluid properties or modal properties vector (m) to be solved, for I number of Gaussian modes, is $$m = [A_i, \mu_{i1}, \mu_{i2}, \sigma_{i1,1}^2, \sigma_{i1,2}^2, \sigma_{i2,2}^2, \ldots, A_I, \mu_{I1}, \mu_{I2}, \sigma_{I1,1}^2, \sigma_{I1,2}^2, \sigma_{I2,2}^2]^T \qquad \text{(Eq. 10)}$$

The nonlinear regularized Levenberg-Marquartz inversion solution is implemented as an iterative gradient-based minimization of the following model, toward solving $\Delta m^k$:

$$\left\| \begin{bmatrix} J(m^k) \\ \lambda^k I \end{bmatrix} \Delta m^k + \begin{bmatrix} e^k \\ \lambda^k I m^k \end{bmatrix} \right\|_2^2 \qquad \text{(Eq. 11)}$$

where k represents the k-th nonlinear iteration; $J(m^k)$ is the k-th Jacobian matrix obtained from the derivative of Eqs. 7-9 with respect to $m^k$; $e^k$ is the k-th misfit vector between Eqs. 7-9 and the actual $T_1$-$T_2$ cross-plot and its total fluid-filled porosity; $m^{k+1} = m^k + \Delta m^k$, where $m^0$ is initial guess obtained by local maxima or inflection of the $T_1$-$T_2$ cross-plot; $\lambda^k$ is the scalar regularization parameter per k-th iteration; and I is an identity matrix. The misfit (e) includes Eqs. 8 and 9 such as to impose a total pore volume constraint.

Selection of $\lambda^k$ is based on the minimum $e^k$ from multiple singular value decomposition (SVD) Tikhonov regularization methods (see Aster et al. 2005) computed in parallel, specifically but not limited to, (1) general cross-validation, (2) general cross-validation of damped SVD, (3) general cross-validation of truncated SVD (4) l-curve corner, (5) l-curve corner of damped SVD, (6) l-curve corner of truncated SVD, and (7) variance of $e^k$. This novel approach of multi-regularization method guarantees a fast convergence to a stable solution because the path to minimum possible misfit is selected at every k-th iteration. The iteration is terminated when $|\|e^k\|_2^2 - \|e^{k-1}\|_2^2| < \varepsilon, \forall k > \in$, where $\varepsilon$ is threshold for change in misfit and $\in$ is minimum number of iterations.

Figure 2B:
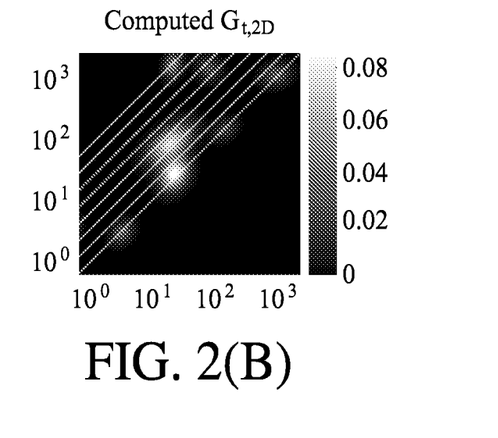
FIG. 2(B) is the recombined approximate $T_1$-$T_2$ cross-plot representation of FIG. 2(A).
Figure 2C:
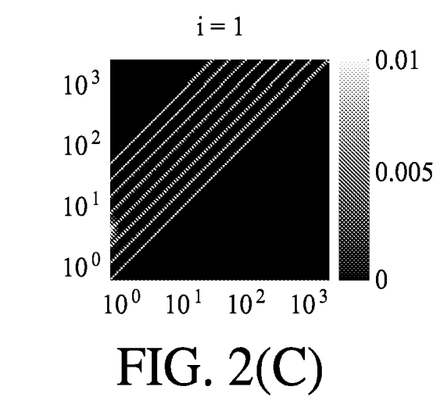
FIGS. 2(C)-2(K) are the plots of the deconvolved individual modes of FIG. 2(A).
Figure 2D:
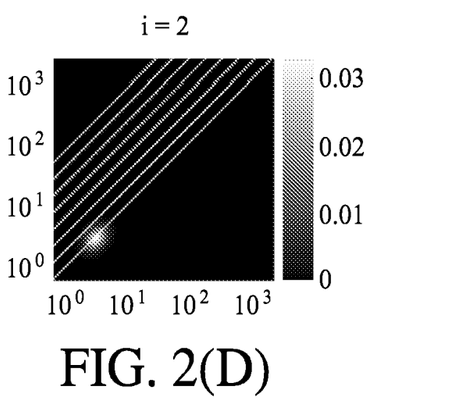
Figure 2E:
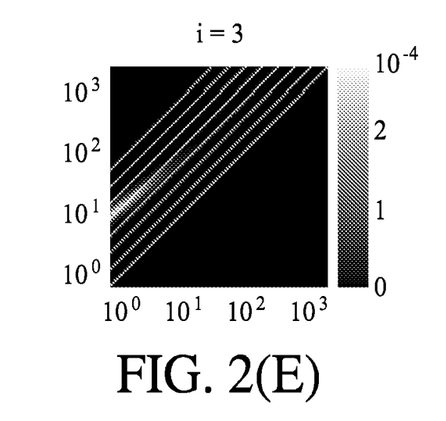
Figure 2F:
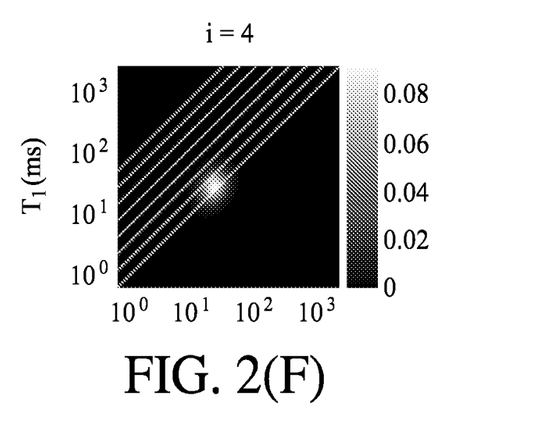
Figure 2G:
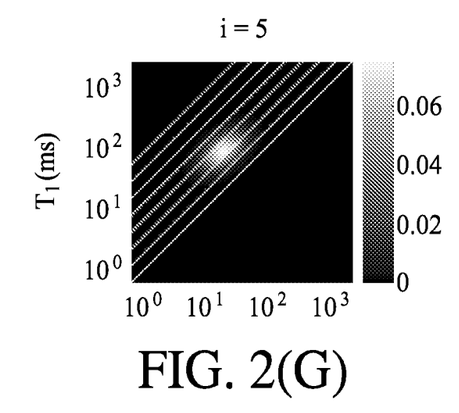
Figure 2H:
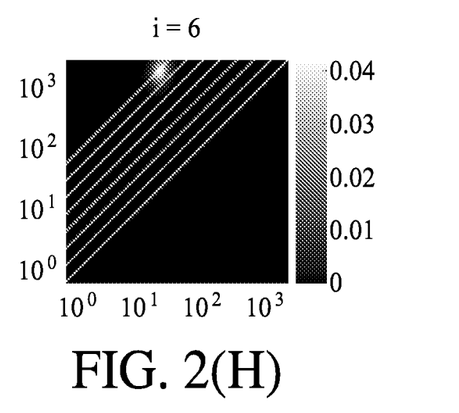
Figure 2I:
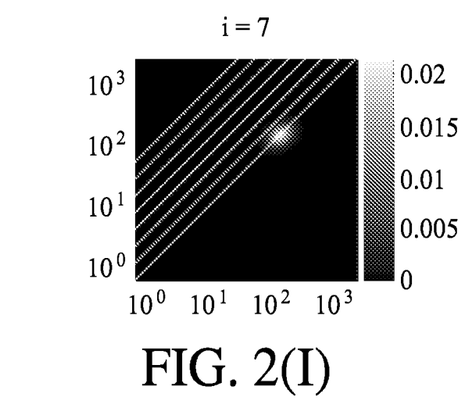
Figure 2J:
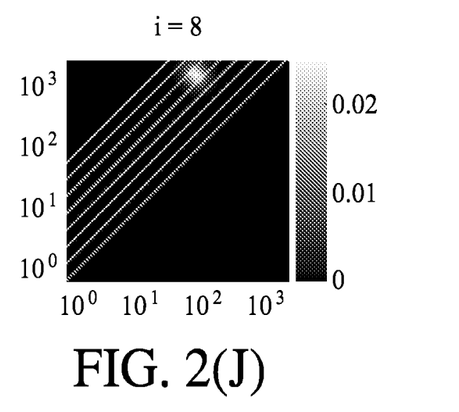
Figure 2K:
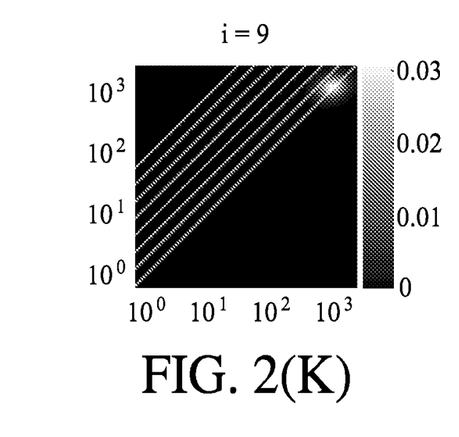

The individual component modes deconvolved by this method are illustrated in FIGS. 2(C)-2(K). FIG. 2(B) is the recombined approximate $T_1$-$T_2$ cross-plot representation of actual $T_1$-$T_2$ in FIG. 2(A).

In this example, the NPPM analysis describes nine different poro-fluid classes that represent distinct combinations of fluid types in pore sizes. The total porosity, $\phi_t$, was determined to be 9.74 p.u. Table 1 summarizes the nine NPPM modes where the poro-fluid class designation is based on the peak $T_{1i}$, peak $T_{2i}$, and peak $T_{1i}/T_{2i}$ ratio. In this example, the multimodal deconvolution or decomposition required less than 0.01 second of CPU time, which illustrates the advantageous speed of the NPPM analyses described herein.

TABLE 1

| Mode number, i | $A_i$, poro-amplitude (p.u.) | Peak $T1_i$ (ms) | Peak $T2_i$ (ms) | Peak $T1_i/T2_i$ ratio | $\phi_i$, fractional pore volume (p.u.) | $S_i$, fractional saturations (%) | $\sigma_{i1,1}^2$ | $\sigma_{i2,2}^2$ | $\sigma_{i2,1}^2 = \sigma_{i1,2}^2$ | poro-fluid class |
|---|---|---|---|---|---|---|---|---|---|---|
| 1 | 0.0124 | 3.98 | 0.53 | 7.54 | 0.06 | 0.62 | 0.0014 | 0.0155 | 0.0001 | Organic matter porosity |
| 2 | 0.0346 | 2.87 | 3.11 | 0.92 | 0.56 | 5.75 | 0.0153 | 0.0171 | 0.0066 | Clay-associated water |
| 3 | 0.0003 | 10.98 | 0.58 | 18.77 | 0.01 | 0.1 | 0.3143 | 0.1995 | 0.2474 | Oil in organic pores |

TABLE 1-continued

| Mode number, i | $A_i$, poro-amplitude (p.u.) | Peak $T1_i$ (ms) | Peak $T2_i$ (ms) | Peak $T1_i/T2_i$ ratio | $\phi_i$, fractional pore volume (p.u.) | $S_i$, fractional saturations (%) | $\sigma_{i1,1}^2$ | $\sigma_{i2,2}^2$ | $\sigma_{i1,2}^2 = \frac{}{\sigma_{i2,1}^2}$ | poro-fluid class |
|---|---|---|---|---|---|---|---|---|---|---|
| 4 | 0.0926 | 32.99 | 26.69 | 1.24 | 2.93 | 30.08 | 0.0251 | 0.0360 | 0.0092 | Water in inorganic pores |
| 5 | 0.0775 | 116.09 | 22.28 | 5.21 | 3.86 | 39.63 | 0.0599 | 0.0489 | 0.0298 | Moveable oil in inorganic pores |
| 6 | 0.0448 | 2978.01 | 25.17 | 118.34 | 0.68 | 6.98 | 0.0098 | 0.0228 | 0.0040 | Macro-porosity or fractures |
| 7 | 0.0222 | 204.23 | 213.04 | 0.96 | 0.39 | 4.01 | 0.0194 | 0.0153 | 0.0068 | Free water |
| 8 | 0.0253 | 2567.95 | 110.72 | 23.19 | 0.53 | 5.44 | 0.0191 | 0.0197 | −0.0014 | Gas in fractures or macro-pores |
| 9 | 0.0318 | 1988.38 | 1795.13 | 1.11 | 0.72 | 7.39 | 0.0276 | 0.0168 | 0.0059 | Free water or free gas |

Figure 2L:
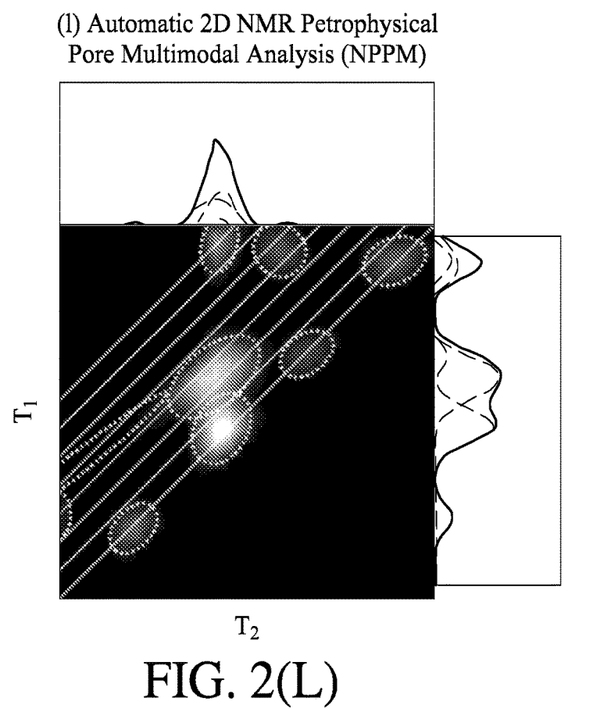
FIG. 2(L) is FIG. 2(A) with overlaid ovular markings to highlight the 9 deconvolved or visually identified modes with, along their respective axes, amplitude as a function of $T_1$ or $T_2$ plot for deconvolved modes (dashed line) and the summation (solid line).

FIG. 2(L) is the data $T_1$-$T_2$ cross-plot with overlaid ovular markings to highlight the 9 deconvolved or visually identified modes with, along their respective axes, amplitude as a function of $T_1$ or $T_2$ plot for deconvolved modes (dashed line) and the summation (solid line). This illustrates the overlap in the distribution of the various modes if only an amplitude is considered as a function of $T_1$ or $T_2$ and not the cross-plot.

Figure 2M:
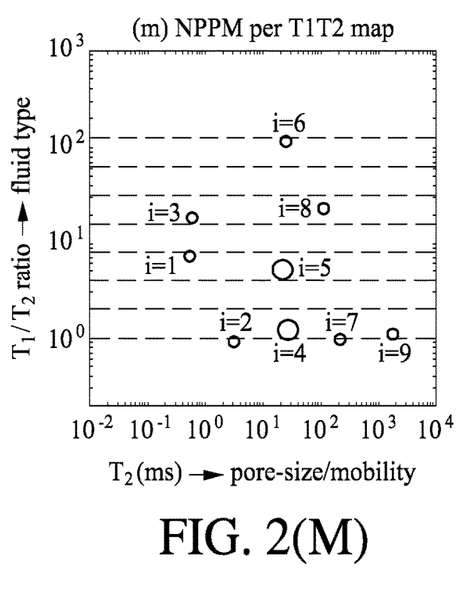
FIGS. 2(M)-2(N) are the modes of FIGS. 2(C)-2(K) replotted as $T_1/T_2$ ratio as a function of $T_2$ and $T_1$, respectively.
Figure 2N:
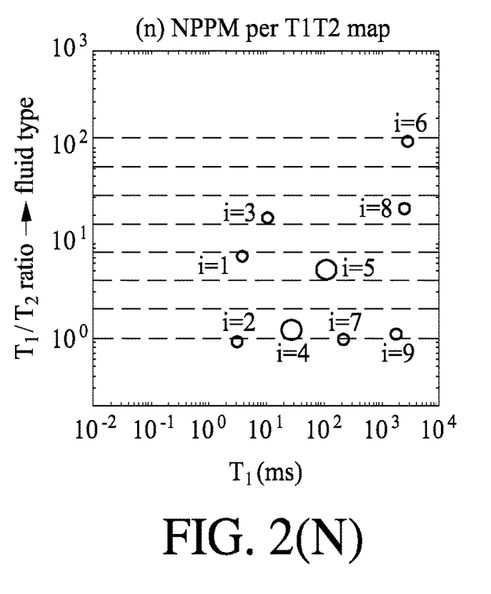

The 9 modes (i=1, 2, ... , 9) are replotted in FIGS. 2(M)-2(N) for modal properties of the $T_1/T_2$ ratio as a function of $T_2$ and $T_1$, respectively, where size of markers is relatively proportional to modal fluid volume for visualization purposes. The $T_1/T_2$ ratio provides insight regarding the fluid type, the $T_2$ data provides insight regarding pore size in which the fluid is located and mobility of the fluid, the $T_1$ data provides insight regarding fluid type, wettability, and other relaxation effects, and the sum of the amplitude for the different modes provides insight regarding the fluid volume that the mode accounts for.

Figure 3A:
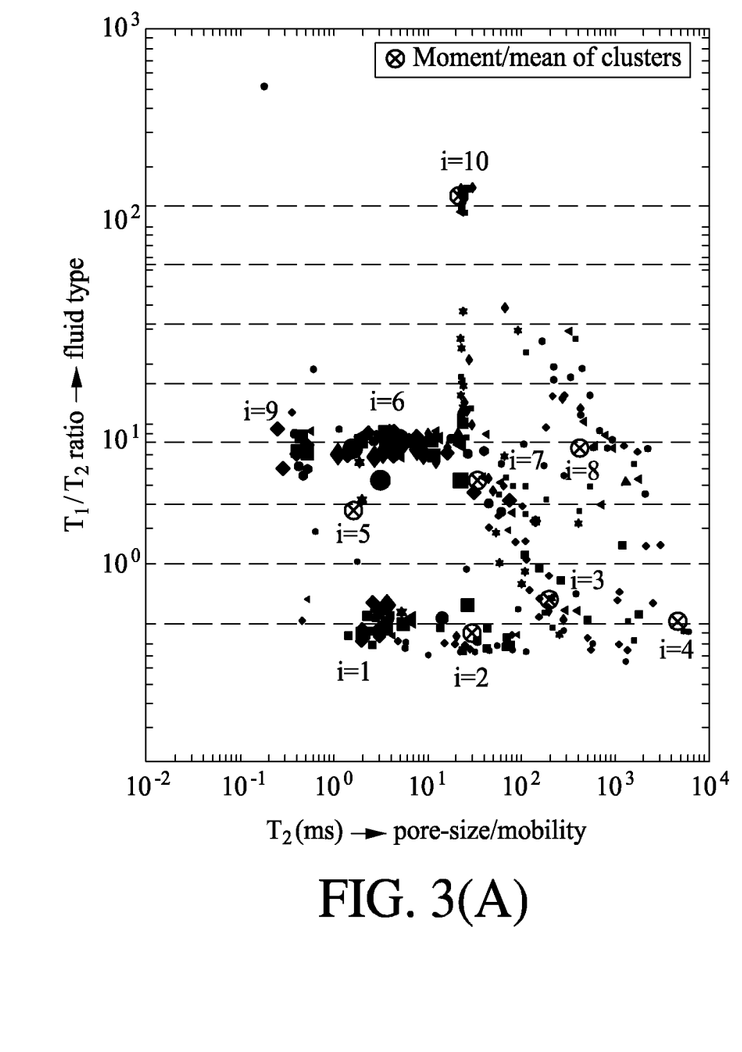
FIGS. 3(A)-3(B) is the overlaid data from several samples plotted as $T_1/T_2$ ratio as a function of $T_2$ and $T_1$ with cluster associations and moments.
Figure 3B:
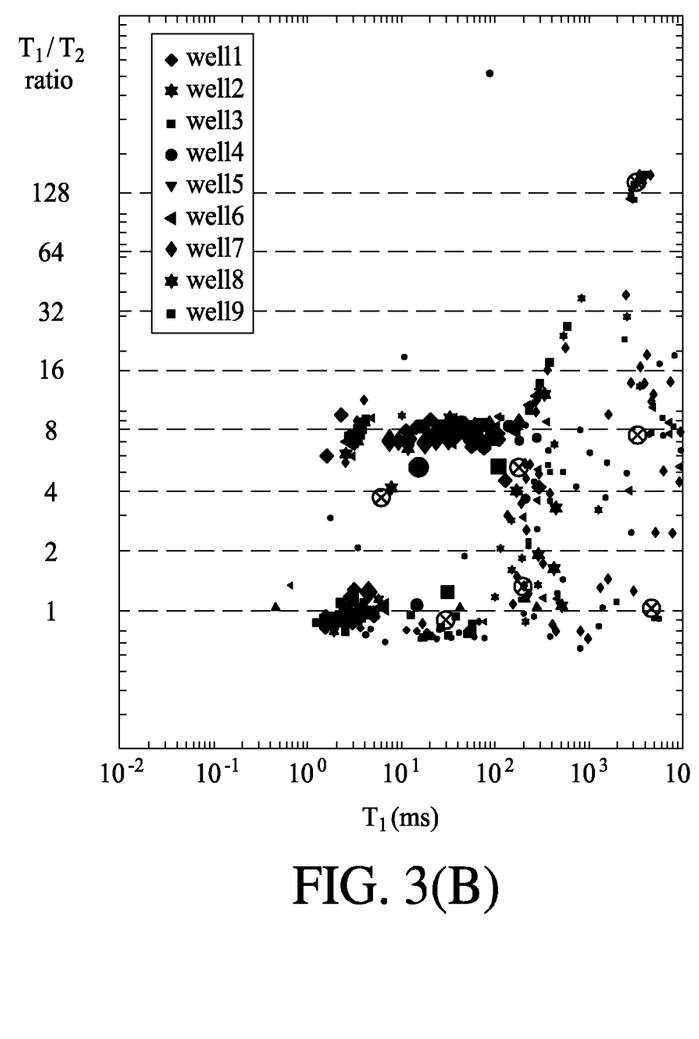

Data for several rock samples at different depths from multiple wells in the same basin were treated the same as above. The data for each rock sample were overlaid and are illustrated in FIGS. 3(A)-3(B) for the $T_1/T_2$ ratio as a function of $T_2$ and $T_1$, respectively. By visual inspection, clusters of the modal properties clearly emerge for samples in this basin. Furthermore, cluster analysis is performed to obtain the most representative cluster associations of modal properties. In this example, 10 cluster associations are obtained, i.e., j=1, 2, ... , 10, and hence 10 corresponding poro-fluid classes can be so defined by one skilled in the art at identifying poro-fluid class definitions based on mean or moment of the clusters' $T_1$, $T_2$, and $T_1/T_2$ ratio. While 10 classes are illustrated in this example, any number of classes (e.g., 1 to 12 or more) can be defined.

Figure 4A:
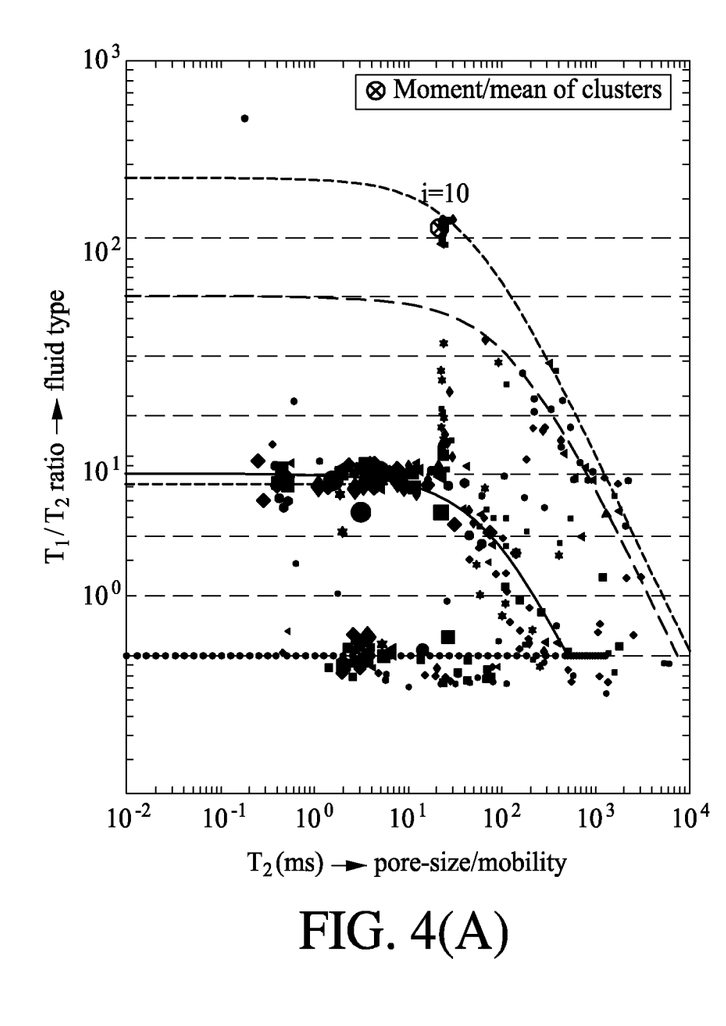
FIGS. 4(A)-4(B) is FIGS. 3(A)-3(B) overlaid with the calibration fits for the analyzed 5 clusters.
Figure 4B:
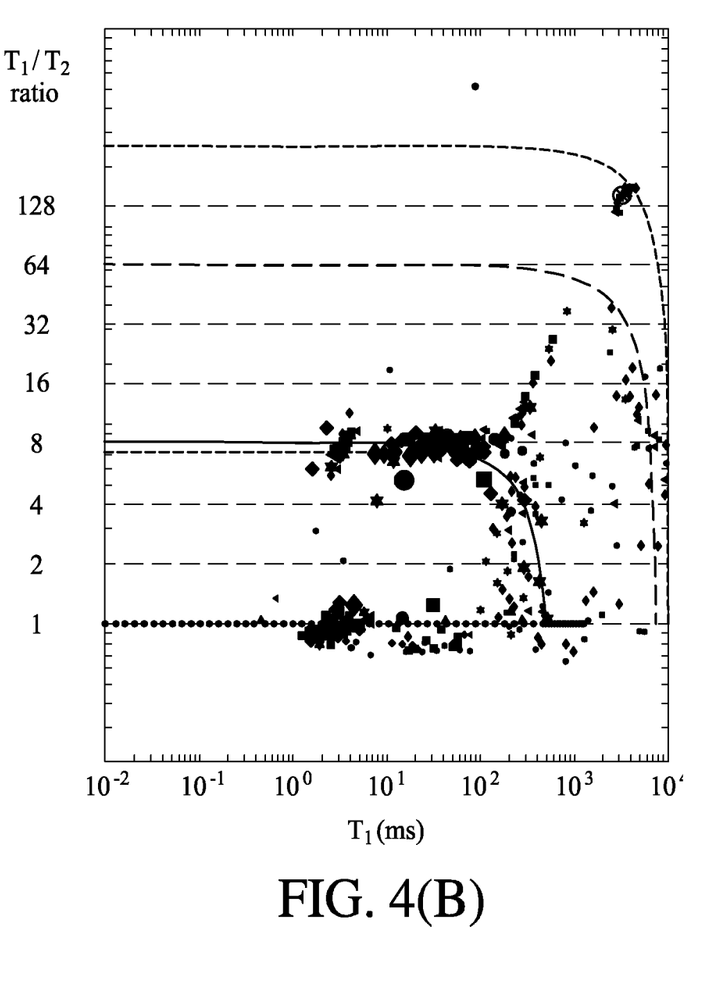

The second portion of the example is a nonlimiting method of performing the methods described herein to achieve the pore and fluid relaxation parameters and endpoints. The analysis as described above was performed where $T_B$ for the 5-analyzed clusters representing 5 possibly different fluid types were initially estimated based on the asymptote in the bulk fluid-dominated relaxation regime with higher $T_{2S}$ in the $T_1/T_2$ ratio as a function of $T_2$ and $T_1$ plots. Subsequently, $T_B$ was iteratively optimized in Eqs. 3-5 with updated solutions of pore and fluid relaxation endpoints for the 5-analyzed fluid types. The results are provided in Table 2. The continuum empirical calibration fits of relaxation mechanisms Eqs. 1-2, for the 5-analysed fluid types, are shown in dashed and solid lines of FIGS. 4(A) and 4(B), i.e., $T_1/T_2$ ratio as a function of $T_2$ and $T_1$ plots, respectively.

TABLE 2

| Clustered fluid, f | Clustered fluid, description | $\rho_2$ (µm/s) | $\rho_1$ (µm/s) | $T_B$ (s) |
|---|---|---|---|---|
| 1 | Water-saturated pores | 2.63 | 2.58 | 2.56 |
| 2 | Oil-saturated pores | 3.2 | 0.39 | 0.50 |
| 3 | Gas-saturated pores | 3.03 | 0.05 | 7.36 |
| 4 | Fluid in organic matter (OM) pores | 150.17 | 20.77 | *N/A |
| 5 | Fluid in macro-pores | 11.23 | 0.04 | 10.51 |

*Relaxation mechanism in OM pores are dominated by homonuclear dipolar coupling such that a bulk fluid relaxation-dominated limit may not be applicable.

Figure 4C:
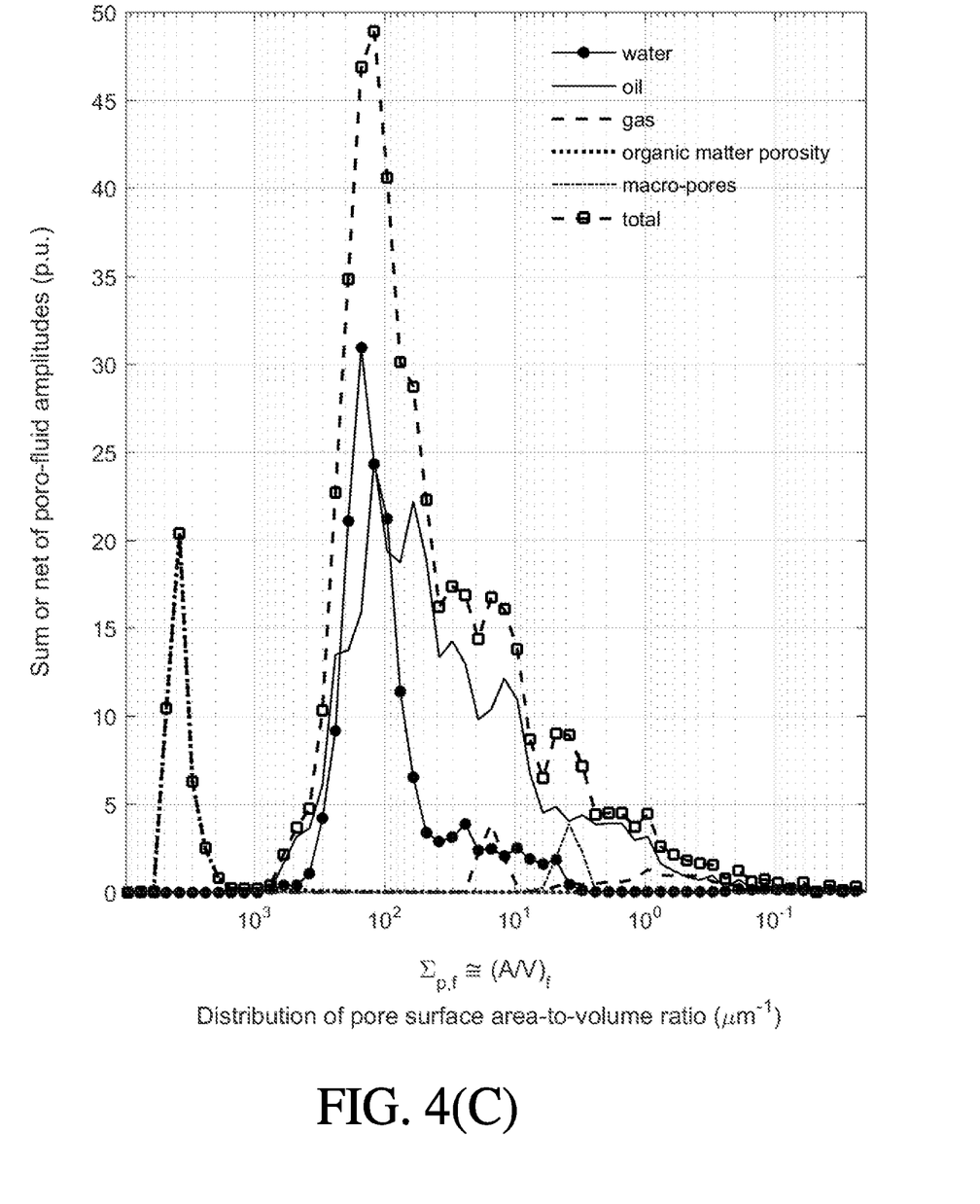
FIG. 4(C) is the distribution of pore surface-to-volume ratio in terms of sum or net NMR signal amplitude as a function of pore surface-to-volume ratio for the 5 clusters analyzed.

FIG. 4(C) is the distribution of pore surface-to-volume ratio, for the 5-analysed clustered fluid types, in terms of sum or net corresponding pore volume using Eq. 6.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

The invention claimed is:

1. A method of improving production of hydrocarbons from a subsurface region, comprising:
    identifying modes in nuclear magnetic resonance (NMR) longitudinal relaxation time ($T_1$)-transverse relaxation time($T_2$) data from a plurality of samples;
    assigning the modes to a poro-fluid class;
    clustering the modes based on poro-fluid class to produce a plurality of clusters, wherein each cluster represents one or more poro-fluid classes;
    estimating a bulk fluid relaxation time (estimated $T_B$) based on an asymptote fit of the clusters, wherein the asymptote is based on $T_1$ and $T_2$ relaxation mechanisms in a bulk fluid relaxation-dominated limit;
    estimating a ratio of a transverse $T_2$ pore surface relaxivity constant ($\rho_2$) to a longitudinal $T_1$ pore surface relaxivity constant ($\rho_1$), the ratio represented as $\rho_2/\rho_1$, based on an asymptote fit of the clusters, wherein the asymptote is based on $T_1$ and $T_2$ relaxation mechanisms in a surface relaxation-dominated limit;
    fitting the $T_1$ relaxation mechanisms and the $T_2$ relaxation mechanisms to one or more of the clusters using the estimated $T_B$;
    deriving at least one pore or fluid relaxation parameter and endpoint for the poro-fluid classes from the fit, wherein the at least one pore or fluid relaxation parameter and endpoint is selected from the group consisting of $\rho_1$, $\rho_2$, a pore surface-to-volume ratio (A/V), an equivalent pore-throat radius ($r_{eq}$), and a bulk fluid relaxation time ($T_B$); and
    identifying potential hydrocarbon-bearing formations in the subsurface region based on the derived at least one pore or fluid relaxation parameter and endpoint for the poro-fluid classes.

2. The method of claim 1 further comprising:
    iteratively (a) calculating the $T_B$ and (b) deriving the fit, wherein the at least one pore or fluid relaxation parameter is based on one of the iteratively derived fits.

3. The method of claim 1 further comprising:
    determining a relative concentration, abundance, and/or net NMR signal amplitude corresponding to clusters as a function of pore size surface-to-volume ratio (A/V) or pore-throat radius ($r_{eq}$).

4. The method of claim 1 further comprising:
    analyzing a newly acquired NMR $T_1$-$T_2$ data for a relative concentration, abundance, and/or net NMR signal amplitude of the clusters as a function of pore size surface-to-volume ratio (A/V) or pore throat radius ($r_{eq}$).

5. The method of claim 1 further comprising:
    calculating a fluid viscosity for each cluster based on the $T_B$;
    calculating a gas-oil ratio for each cluster based on the $T_B$;
    calculating rock permeability for each cluster based on the pore size surface-to-volume ratio (A/V) or pore-throat radius ($r_{eq}$); and
    determining rock mineralogy and wettability for each cluster based on the longitudinal $T_1$ pore surface relaxivity constant ($\rho_1$) and transverse $T_2$ pore surface relaxivity constant ($\rho_2$).

6. The method of claim 3, wherein the NMR $T_1$-$T_2$ data is collected in a rock sample, wherein the rock sample is a core sample from a subterranean formation, and the method further comprises managing hydrocarbons based at least in part upon the determined relative concentration, abundance, and/or net NMR signal amplitude.

7. The method of claim 6, wherein managing hydrocarbons comprises one or more of:
    identifying a zone of the subterranean formation for completion, and causing one or more completion operations to be carried out on the identified zone;
    identifying a portion of the subterranean formation from where to obtain a core sample for further analysis, and obtaining one or more core samples from the identified portion;
    causing a simulation or completion operation to be carried out on the subterranean formation; and/or
    identifying a horizontal well landing location within the subterranean formation, and causing a horizontal well to be drilled to the identified landing location.

8. The method of claim 5, wherein the NMR $T_1$-$T_2$ data is collected in a rock sample, wherein the rock sample is a core sample from a subterranean formation, and the method further comprises managing hydrocarbons based at least in part upon the calculated fluid viscosity or gas-oil ratio for each cluster, the calculated rock permeability for each cluster, and the determined rock mineralogy and wettability for each cluster.

9. The method of claim 8, wherein managing hydrocarbons comprises one or more of:
    identifying a zone of the subterranean formation for completion, and causing one or more completion operations to be carried out on the identified zone;
    identifying a portion of the subterranean formation from where to obtain a second core sample for further analysis, and obtaining the second core sample from the identified portion;
    causing a simulation or completion operation to be carried out on the subterranean formation; and/or
    identifying a horizontal well landing location within the subterranean formation, and causing a horizontal well to be drilled to the identified landing location.

10. The method of claim 1, wherein clustering the modes for each poro-fluid class comprises:
    identifying modes in the NMR T1-T2 data by manual analysis or visual inspection.

11. The method of claim 1, wherein clustering the modes for each poro-fluid class comprises:
    identifying modes in the NMR T1-T2 data with a multimodal deconvolution or decomposition with regularized nonlinear inversion;
    deriving a modal properties vector comprising modal properties for each of the modes;
    performing a cluster analysis of the modes to identify clusters; and
    assigning the poro-fluid class to the clusters based on one or more of the modal properties of the modes in each of the clusters.

12. The method of claim 11, wherein the multimodal deconvolution or decomposition is selected from the group consisting of Gaussian, Lorentzian, Voigt, exponentially modified Gaussian, and any variation thereof.

13. The method of claim 11, wherein the regularized nonlinear inversion is selected from the group consisting of Gauss-Newton inversion, Landweber inversion, Levenberg-Marquartz inversion, Occam's inversion, and any variation thereof.

14. The method of claim 11, wherein the nonlinear regularization inversion is an iterative calculation of multiple regularizations where the regularization in each iteration having a minimum misfit proceeds to the next iteration.

15. The method of claim 1, wherein the poro-fluid classes are selected from the group consisting of free fluid, fluid in pores, fluid in macroporosity or fractures, fluid in inorganic pores, fluid in organic pores, free liquid, liquid in pores, liquid in macroporosity or fractures, liquid in inorganic pores, liquid in organic pores, free gas, gas in pores, gas in macroporosity or fractures, gas in inorganic pores, gas in organic pores, free oil, oil in pores, oil in macroporosity or fractures, oil in inorganic pores, oil in organic pores, free water, water in pores, water in macroporosity or fractures, water in inorganic pores, water in organic pores, clay-associated water, clay-bound water, surface relaxation-dominated fluid, surface relaxation-dominated oil, surface relaxation-dominated water, bulk relaxation-dominated fluid, bulk relaxation-dominated oil, bulk relaxation-dominated water, bulk relaxation-dominated gas, bound fluid, bound oil, bound water, capillary-bound fluid, capillary-bound water, capillary-bound oil, bitumen and any combination thereof.

16. The method of claim 1, wherein the NMR $T_1$-$T_2$ data is for fluids in a plurality of core samples from a subterranean formation.

17. The method of claim 1, wherein the NMR $T_1$-$T_2$ is from NMR logging data for fluids in a subterranean formation.

18. The method of claim 1, wherein the NMR $T_1$-$T_2$ is for fluids in a synthetic core sample.

19. The method of claim 1 further comprising:
  performing a NMR logging operation for a subterranean formation;
  deriving the at least one pore and fluid relaxation parameter for the poro-fluid classes from a first portion of the NMR logging operation in real-time; and
  analyzing a newly acquired NMR $T_1$-$T_2$ data for a second portion of the NMR logging operation based on the at least one pore and fluid relaxation parameter for the poro-fluid classes.

20. A computing device for improving the production of hydrocarbons in a subsurface region, comprising:
  a processor;
  a memory coupled to the processor; and
  instructions provided to the memory, wherein the instructions are executable by the processor and are configured to:
    identify modes in nuclear magnetic resonance (NMR $T_1$-$T_2$) data from a plurality of samples;
    assign the modes to a poro-fluid class;
    cluster the modes based on poro-fluid class to produce a plurality of clusters, wherein each cluster represents one or more poro-fluid classes;
    estimate a bulk fluid relaxation time (estimated $T_B$) based on an asymptote fit of the clusters, wherein the asymptote is based on $T_1$ and $T_2$ relaxation mechanisms in a bulk fluid relaxation-dominated limit;
    estimate a ratio of a transverse $T_2$ pore surface relaxivity constant ($\rho_2$) to a longitudinal $T_1$ pore surface relaxivity constant ($\rho_1$), the ratio represented as $\rho_2/\rho_1$, based on an asymptote fit of the clusters, wherein the asymptote is based on $T_1$ and $T_2$ relaxation mechanisms in a surface relaxation-dominated limit;
    fit the $T_1$ relaxation mechanisms and the $T_2$ relaxation mechanisms to one or more of the clusters using the estimated $T_B$;
  derive at least one pore or fluid relaxation parameter and endpoint for the poro-fluid classes from the fit, wherein the at least one pore or fluid relaxation parameter and endpoint is selected from the group consisting of $\rho_1$, $\rho_2$, a pore surface-to-volume ratio (A/V), an equivalent pore-throat radius ($r_{eq}$), and a bulk fluid relaxation time ($T_B$); and
  identify potential hydrocarbon-bearing formations in the subsurface region based on the derived at least one pore or fluid relaxation parameter and endpoint for the poro-fluid classes.

* * * * *